(12) United States Patent
Fang et al.

(10) Patent No.: US 10,758,723 B2
(45) Date of Patent: Sep. 1, 2020

(54) NERVE CUFF ELECTRODE FOR NEUROMODULATION IN LARGE HUMAN NERVE TRUNKS

(71) Applicant: Neuros Medical, Inc., Willoughby Hills, OH (US)

(72) Inventors: Zi-Ping Fang, Beachwood, OH (US); Nemath Syed Shah, Cleveland Heights, OH (US)

(73) Assignee: Neuros Medical, Inc., Willoughby Hills, OH (US)

( * ) Notice: Subject to any disclaimer, the term of this patent is extended or adjusted under 35 U.S.C. 154(b) by 444 days.

(21) Appl. No.: 15/510,824

(22) PCT Filed: Sep. 12, 2014

(86) PCT No.: PCT/US2014/055374
§ 371 (c)(1),
(2) Date: Mar. 13, 2017

(87) PCT Pub. No.: WO2016/039768
PCT Pub. Date: Mar. 17, 2016

(65) Prior Publication Data
US 2017/0246453 A1 Aug. 31, 2017

Related U.S. Application Data

(63) Continuation-in-part of application No. 14/276,200, filed on May 13, 2014, now Pat. No. 8,983,612,
(Continued)

(51) Int. Cl.
*A61N 1/05* (2006.01)
*A61N 1/36* (2006.01)

(52) U.S. Cl.
CPC ....... *A61N 1/0556* (2013.01); *A61N 1/36007* (2013.01); *A61N 1/36057* (2013.01);
(Continued)

(58) Field of Classification Search
CPC .............. A61N 1/0556; A61N 1/36007; A61N 1/36057; A61N 1/36071; A61N 1/36153; A61N 1/36157; A61N 1/36171
See application file for complete search history.

(56) References Cited

U.S. PATENT DOCUMENTS 3,738,368 A 6/1973 Avery et al.
4,155,366 A 5/1979 Di Mucci
(Continued)

FOREIGN PATENT DOCUMENTS

CN 102573986 A 7/2012
DE 202010015346 U1 4/2011
(Continued)

OTHER PUBLICATIONS

Ackermann et al.; Effect of bipolar cuff electrode design on block thresholds in high-frequency electrical neural conduction block; IEEE Transactions on Neural Systems and Rehabilitation Engineering; 17(5); pp. 469-477; Oct. 1, 2009.
(Continued)

*Primary Examiner* — Catherine M Voorhees
*Assistant Examiner* — Roland Dinga
(74) *Attorney, Agent, or Firm* — Shay Glenn LLP

(57) ABSTRACT

A durable nerve cuff electrode for achieving block of an action potential in a large diameter nerve.

26 Claims, 11 Drawing Sheets

Related U.S. Application Data which is a continuation of application No. 13/474,926, filed on May 18, 2012, now Pat. No. 8,731,676.

(60) Provisional application No. 61/487,877, filed on May 19, 2011.

(52) U.S. Cl.
CPC ..... *A61N 1/36071* (2013.01); *A61N 1/36153* (2013.01); *A61N 1/36157* (2013.01); *A61N 1/36171* (2013.01)

(56) References Cited

U.S. PATENT DOCUMENTS

| | | | |
|---|---|---|---|
| 4,573,481 A | 3/1986 | Bullara | |
| 4,602,624 A | 7/1986 | Naples et al. | |
| 4,979,511 A | 12/1990 | Terry, Jr. | |
| 5,143,067 A | 9/1992 | Rise et al. | |
| 5,324,322 A | 6/1994 | Grill et al. | |
| 5,653,739 A | 8/1997 | Maurer et al. | |
| 5,755,750 A | 5/1998 | Petruska | |
| 5,964,702 A | 10/1999 | Grill, Jr. et al. | |
| 6,292,703 B1* | 9/2001 | Meier | A61B 5/0422 607/118 |
| 6,456,866 B1 | 9/2002 | Tyler et al. | |
| 6,699,275 B1 | 3/2004 | Knudson et al. | |
| 6,836,685 B1 | 12/2004 | Fitz | |
| 6,860,851 B2 | 3/2005 | Knudson et al. | |
| 7,167,750 B2 | 1/2007 | Knudson et al. | |
| 7,201,757 B2 | 4/2007 | Knudson et al. | |
| 7,292,890 B2 | 11/2007 | Whitehurst et al. | |
| 7,389,145 B2 | 6/2008 | Kilgore et al. | |
| 7,444,183 B2 | 10/2008 | Knudson et al. | |
| 7,783,362 B2 | 8/2010 | Whitehurst et al. | |
| 7,860,570 B2 | 12/2010 | Whitehurst et al. | |
| 8,060,208 B2 | 11/2011 | Kilgore et al. | |
| 8,108,052 B2 | 1/2012 | Boling | |
| 8,116,882 B2 | 2/2012 | Kowalczewski | |
| 8,170,675 B2 | 5/2012 | Alataris et al. | |
| 8,600,505 B2 | 12/2013 | Libbus et al. | |
| 8,731,676 B2 | 5/2014 | Fang et al. | |
| 8,983,612 B2 | 3/2015 | Fang et al. | |
| 9,295,841 B2 | 3/2016 | Fang et al. | |
| 9,884,192 B2 | 2/2018 | Kilgore et al. | |
| 2002/0055779 A1 | 5/2002 | Andrews | |
| 2002/0198572 A1 | 12/2002 | Weiner | |
| 2003/0144709 A1 | 7/2003 | Zabara et al. | |
| 2004/0111139 A1* | 6/2004 | McCreery | A61N 1/0556 607/117 |
| 2004/0243182 A1 | 12/2004 | Cohen et al. | |
| 2005/0131485 A1 | 6/2005 | Knudson et al. | |
| 2005/0143789 A1 | 6/2005 | Whitehurst | |
| 2005/0149154 A1 | 7/2005 | Cohen et al. | |
| 2006/0030919 A1 | 2/2006 | Mrva et al. | |
| 2006/0195158 A1 | 8/2006 | Cory | |
| 2006/0270944 A1 | 11/2006 | King et al. | |
| 2006/0271137 A1* | 11/2006 | Stanton-Hicks | A61N 1/0551 607/118 |
| 2006/0293721 A1 | 12/2006 | Tarver et al. | |
| 2008/0027505 A1 | 1/2008 | Levin et al. | |
| 2008/0046055 A1 | 2/2008 | Durand et al. | |
| 2008/0086180 A1 | 4/2008 | Ben-Ezra et al. | |
| 2008/0172116 A1 | 7/2008 | Mrva et al. | |
| 2008/0183226 A1 | 7/2008 | Buras et al. | |
| 2008/0228194 A1 | 9/2008 | Westlund et al. | |
| 2008/0294221 A1 | 11/2008 | Kilgore et al. | |
| 2008/0319511 A1 | 12/2008 | Pless | |
| 2009/0069738 A1 | 3/2009 | Rossing et al. | |
| 2009/0083070 A1 | 3/2009 | Giftakis et al. | |
| 2009/0204173 A1 | 8/2009 | Fang et al. | |
| 2009/0281595 A1 | 11/2009 | King et al. | |
| 2010/0121408 A1 | 5/2010 | Imran et al. | |
| 2010/0152808 A1 | 6/2010 | Boggs, II | |
| 2010/0168820 A1 | 7/2010 | Maniak et al. | |
| 2010/0211135 A1 | 8/2010 | Caparso et al. | |
| 2010/0241190 A1 | 9/2010 | Kilgore et al. | |
| 2010/0274312 A1 | 10/2010 | Alataris et al. | |
| 2010/0274314 A1 | 10/2010 | Alataris et al. | |
| 2010/0274315 A1 | 10/2010 | Alataris et al. | |
| 2010/0274316 A1 | 10/2010 | Alataris et al. | |
| 2010/0274317 A1 | 10/2010 | Parker et al. | |
| 2010/0274318 A1 | 10/2010 | Walker et al. | |
| 2010/0274326 A1 | 10/2010 | Chitre et al. | |
| 2011/0071593 A1 | 3/2011 | Parker et al. | |
| 2011/0077721 A1 | 3/2011 | Whitehurst et al. | |
| 2011/0230701 A1 | 9/2011 | Simon et al. | |
| 2012/0016439 A1 | 1/2012 | Alataris et al. | |
| 2012/0083709 A1 | 4/2012 | Parker et al. | |
| 2012/0089199 A1 | 4/2012 | Bolea et al. | |
| 2012/0253261 A1 | 10/2012 | Poletto et al. | |
| 2013/0289667 A1 | 10/2013 | Wacnik et al. | |
| 2014/0228905 A1 | 8/2014 | Bolea | |
| 2014/0249597 A1 | 9/2014 | Fang et al. | |
| 2015/0230809 A1 | 8/2015 | Becker | |
| 2017/0095667 A1 | 4/2017 | Yakovlev et al. | |
| 2017/0239486 A1 | 8/2017 | Suryavanshi | |
| 2017/0319381 A1 | 11/2017 | Rogers | |
| 2017/0333701 A1 | 11/2017 | Bradley et al. | |
| 2018/0043172 A1 | 2/2018 | Serrano Carmona | |
| 2018/0085587 A1 | 3/2018 | Kilgore et al. | |
| 2019/0374779 A1 | 12/2019 | Kilgore et al. | |

FOREIGN PATENT DOCUMENTS

| | | |
|---|---|---|
| JP | 2009522015 A | 6/2009 |
| WO | WO00/61222 A1 | 10/2000 |
| WO | 2005/105202 | 11/2005 |
| WO | WO2005/105202 A1 | 11/2005 |
| WO | 2009/058258 | 5/2009 |
| WO | WO2009/079270 A1 | 6/2009 |
| WO | WO2012/159002 A8 | 11/2012 |

OTHER PUBLICATIONS

Ackermann et al.; Electrical conduction block in large nerves: high frequency current delivery in the nonhuman primate; Muscle and Nerve. 43(6); pp. 897-899; Jun. 2011.

Becker et al.; Essentials of local anesthetic pharmacology; Anesthesia progress; 53(3); pp. 98-109; Sep. 2006.

Bhadra et al.; High-frequency electrical conduction block of mammalian peripheral motor nerve; Muscle and Nerve; 32(6); pp. 782-790; Dec. 2005.

Bhadra et al.; Simulation of high-frequency sinusoidal electrical block of mammalian myelinated axons; Journal of Computational Neuroscience; 22(3); pp. 313-326; Jun. 1, 2007.

Bouaziz et al.; Neurologic complication of peripheral neural blockade. In Cousins and Bridenbaugh's Neural blockade in clinical anesthesia and pain medicine, 4th ed. (Cousins et al., eds.); Ch. 20; Lippincott Williams and Wilkins; pp. 464-477; (year of pub sufficiently earlier than effective US filing date and any foreign priority date) 2009.

Cleeland et al.; Pain assessment: global use of the Brief Pain Inventory; Annals, Academy of Medicine, Singapore; 23(2); pp. 129-138; Mar. 1994.

Dickinson et al.; Maldynia; pathophysiology and management of neuropathic and maladaptive pain'a report of the AMA Council on Science and Public Health; Pain Medicine; 11(11); pp. 1635-1653; Nov. 1, 2010.

Dworkin et al.; Interpreting the clinical importance of treatment outcomes in chronic pain clinical trials: IMMPACT recommendations; The Journal of Pain; 9(2); pp. 105-121; Feb. 1, 2008.

Fisher et al.; Chronic stability and selectivity of four-contact spiral nerve-cuff electrodes in stimulating the human femoral nerve; J. Neural Eng.; 6(4); pp. 1-16; Aug. 2009.

Flor et al.; Phantom limb pain: a case of maladaptive CNS plasticity? Nature Reviews Neuroscience; 7(11); pp. 873-881; Nov. 2006.

Fyfe, N.; An audit of amputation levels in patients referred for prosthetic rehabilitation; Prosthetics and Orthotics International; 14(2); pp. 67-70; Aug. 1990.

(56) References Cited

OTHER PUBLICATIONS

Gerges et al.; Frequency-and amplitude-transitioned waveforms mitigate the onset response in high-frequency nerve block; Journal of Neural Engineering; 7(6); pp. 1-17; Dec. 2010.
Guse et al.; Outcomes of the surgical treatment of peripheral neuromas of the hand and forearm: a 25-year comparative outcome study; Annals of plastic surgery; 71(6); pp. 654-658; (abstract) Dec. 1, 2013.
Hadzic et al.; Neurologic complications of peripheral nerve blocks. In Peripheral nerve blocks: principles and practice, 3rd ed. (Hadzic and Vloka, eds.); Ch. 6; New York: McGraw-Hill; pp. 67-77; Sep. 20, 2004.
Haroutounian et al.; Primary afferent input critical for maintaining spontaneous pain in peripheral neuropathy; PAIN; 155(7); pp. 1272-1279 (abstract); Jul. 1, 2014.
Hsu et al.; Postamputation pain: epidemiology, mechanisms, and treatment; Journal of Pain Research; 6; pp. 121-136; Feb. 12, 2013.
Keller et al.; Validity of the brief pain inventory for use in documenting the outcomes of patients with noncancer pain; The Clinical Journal of Pain; 20(5); pp. 309-318; Sep. 1, 2004.
Kilgore et al.; Nerve conduction block utilizing high-frequency alternating current; Med. Biol. Eng. Comput.; 42(3); pp. 394-406; May 1, 2004.
Kilgore et al.; Reversible nerve conduction block using kilohertz frequency alternating current; Neuromodulation: Technology at the Neural Interface; 17(3); pp. 242-255; Apr. 2014.
Kumar et al.; Spinal cord stimulation versus conventional medical management for neuropathic pain: A multicentre randomised controlled trial in patients with failed back surgery syndrome; Pain; 132(1-2); pp. 179-188; Nov. 1, 2007.
Leland et al.; American war and military operations casualties: lists and statistics. Congressional Research Service; CRS Report to Congress; RL32492; pp. 1-30; Feb. 26, 2010.
Lewin-Kowalik et al.; Prevention and management of painful neuroma; Neurol Med Chir (Tokyo); 46(2); pp. 62-68; Feb. 2006.
Melzack et al.; Pain mechanisms: a new theory; Science; 150(3699); pp. 971-979; Nov. 19, 1965.
Naples et al.; A spiral nerve cuff electrode for peripheral nerve stimulation; IEEE Transactions on Biomedical Engineering; 35(11); pp. 905-916; Nov. 1988.
Narang et al.; Functional capabilities of lower limb amputees; Prosthetics and Orthotics International; 8(1); pp. 43-51; Jan. 1, 1984.
NLLIC Staff. Fact Sheet. Amputation Statistics by Cause Limb Loss in the United States. Amputee Coalition of America (2008) 2 pages; retrieved from internet site http://www.amputee-coalitionsorg/fact_sheets/amp_stats_cause.pdf: Accessed Aug. 26, 2014; (year of pub sufficiently earlier than effective US filing date and any foreign priority date) 2008.

North et al.; Spinal cord stimulation versus re-operation in patients with failed back surgery syndrome: an international multicenter randomized controlled trial (Evidence study); Neuromodulation: Technology at the Neural Interface; 14(4); pp. 330-336; Jul. 2011.
Page et al.; Oral Posters—Intrathecal Drug Delivery for Pain and Spasticity: 2013 1630-1640; Spine; Jun. 11, 004. Effect of intrathecal intermittent boluses and morphine concerntration on the incidence of inflammatory mass in a canine model; International Modulation Society; pp. 272-273; Jun. 11, 2013.
Pohjolainen et al.; Prosthetic use and functional and social outcome following major lower limb amputation: Prosthetics and Orthotics Intl.; 14(2); pp. 75-79; Jan. 1, 1990.
Polasek et al.; Stimulation stability and selectivity of chronically implanted multicontact nerve cuff electrodes in the human upper extremity; IEEE Transactions on Neural Systems and Rehabilitation Engineering; 17(5); pp. 428-437; Oct. 2009.
Saper et al.; Occipital nerve stimulation for the treatment of intractable chronic migraine headache: ONSTIM feasibility study; Cephalalgia; 31(3); pp. 271-285; Feb. 2011.
Schoppen et al.; Physical, mental, and social predictors of functional outcome in unilateral lower-limb amputees; Arch Phys Med Rehabil; 84(6); pp. 803-811; Jun. 1, 2003.
Soin et al.; High-frequency electrical nerve block for post amputation pain: a pilot study; Neuromodulation; 16(5); 9 pages; Sep. 1, 2013.
Soin et al.; Feasibility study on high-frequency electrical nerve block for amputation pain; Neuromodulation; 14(6); p. 561; Nov. 1, 2011.
Subedi et al.; Phantom limb pain: mechanisms and treatment approaches; Pain Research and Treatment; Article ID 664605; 8 pages; (year of pub sufficiently earlier than effective US filing date and any foreign priority date) 2011.
Vaso et al.; Peripheral nervous system origin of phantom limb pain; Pain; 155(7); pp. 1384-1391; Jul. 1, 2014.
Waataja et al.; Effects of high-frequency alternating current on axonal conduction through the vagus nerve; J. Neural Eng.; 8(5); pp. 1-7; Sep. 15, 2011.
Ziegler-Graham et al.; Estimating the Prevalence of Limb Loss in the United States: 2005 to 2050; Arch Phys Med Rehabil; 89(3); pp. 422-429; Mar. 1, 2008.
International Search Report and Written Opinion; Application No. PCT/US2014/055374, dated May 21, 2015 (11 pages).
Extended European Search Report; Application No. EP12786360.3, dated Sep. 19, 2014 (7 pages).
International Preliminary Report on Patentability, Application No. PCT/US2014/055374, dated Mar. 14, 2017 (6 pages).
Sikka; Facial expression analysis for estimating pain in clinical settings; In Proceedings of the 16th International Conference on Multimodal Interaction; pp. 349-353; Nov. 2014.
Syed Shah et al.; U.S. Appl. No. 16/379,053 entitled "Apparatuses and methods for setting an electrical dose," filed Apr. 9, 2019.

* cited by examiner

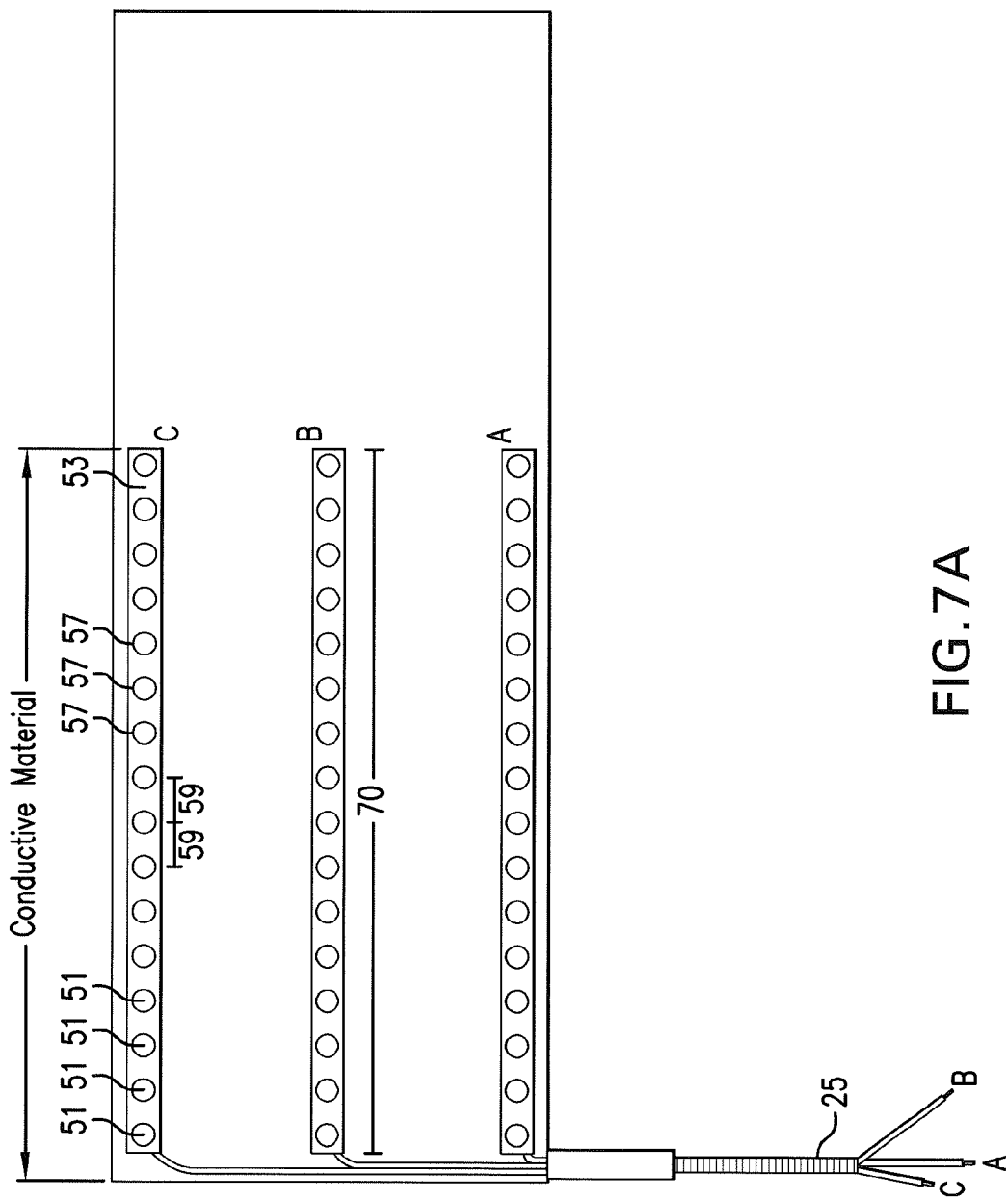

FIG 8: Summary of Feasibility Study Results
Electrical Nerve Block for Amputation Pain

| Subject | 1 | 2 | 3 | 4 | 5 |
|---|---|---|---|---|---|
| Gender, age | Male, 37 | Male, 54 | Female, 53 | Male, 76 | Male, 52 |
| Cause of amputation | Dysvascular | Dysvascular | Infection | Trauma | Trauma |
| Level of Amputation | Below knee | Above knee | Above knee | Below knee | Above knee |
| Nerve blocked | Tibial | Sciatic | Sciatic | Tibial | Sciatic |
| Spontaneous pain intensity at each visit | 3, 3, 3 | 0, 0, 0, 0 | 0, 0 | 2, 3, 7, 7 | 0, 7, 7 |
| Induced pain intensity by pressing the neuroma | Not tried | 9 | 7 | 5 | 8 |
| In-clinic test result: number of sessions with significant/partial/no pain reductions | 1/2/5 | 3/1/2 | 0/3/1 | 6/1/0 | 7/0/0 |
| At-home use result: number of sessions with significant/partial/no pain reductions | 0/0/1 | Not used | Not used | 13/0/0 | 4/0/0 |
| Conclusion | Success in clinic | Success in clinic | Not successful | Complete success | Complete success |

NERVE CUFF ELECTRODE FOR NEUROMODULATION IN LARGE HUMAN NERVE TRUNKS

This application is related to pending U.S. patent application Ser. No. 14/276,200 filed May 13, 2014; which is a continuation of U.S. patent application Ser. No. 13/474,926 filed May 18, 2012 now U.S. Pat. No. 8,731,676; which claims priority to U.S. patent application Ser. No. 61/487,877 filed May 19, 2011, each of which is expressly incorporated by reference herein in its entirety.

A nerve cuff electrode with a plurality of segmented platinum contacts connected by at least one wire made of durable and biocompatible conductive material fashioned in a helical configuration. In embodiments, two such wires fashioned in a helical configuration provided redundancy. The helical configuration increased the durability of the interconnections relative to a non-helical wire or a straight wire. The inventive nerve cuff electrode provided enhanced durability, lasting on the order of 1,000,000 cycles of compression of up to 50% of diameter followed by uncompression to original diameter, compared to standard electrodes that disintegrated or broke after compression cycles on the order of 100,000 cycles. Durability is a particular problem, solved by the inventive apparatus and method, when electrodes in use are used on relatively large nerve trunks in the lower extremities, generally defined as a nerve trunk having a diameter of 3 mm or greater. This is due to repeated creasing, wrinkling, and/or breaking along their length, occurring for example when the nerve trunk is repeatedly flattened and compressed during a patient's daily activities.

The inventive nerve cuff electrode comprises a plurality of conductive nerve contact segments, with the segments having an inner surface contacting a nerve trunk and an outer surface not contacting the nerve trunk; at least a single wire of a conductive biocompatible material operatively connecting the plurality of conductive nerve contact segments thus forming a segmented strip, the wire configured as helical portions separated by non-helical portions where the non-helical portions are secured to the surface of the conductive nerve contact segments not contacting the nerve trunk; and a conductive lead capable of operatively connecting a waveform generator to at least one of the plurality of nerve contact segments. The wire helical portions are along the wire length between the conductive nerve contact segments, and the wire non-helical portions are secured to the conductive nerve contact segments by a plurality of spot welds. The wire helical portions are embedded in a non-conductive material. The helical portions are separated by non-helical portions that connects the conductive nerve contact segments. A second wire may operatively connect the plurality of nerve contact segments, with the second wire generally parallel with the first wire. In one embodiment, the conductive nerve contact segments are platinum, the wires are stainless steel, and the non-conductive material is silicone.

In one embodiment the nerve cuff electrode comprises a plurality of platinum nerve contact segments, each nerve contact segment comprising an inner surface contacting a nerve trunk and an outer surface not contacting the nerve trunk; at least two wires of a conductive biocompatible material operatively connecting the plurality of platinum nerve contact segments thus forming a segmented strip, the wires configured as helical portions separated by non-helical portions where the non-helical portions connect to the surface of the platinum nerve contact segments not contacting the nerve trunk by a plurality of spot welds, the wires embedded in a silicone sheet such that only the inner surface of the platinum nerve contact segments contacts the nerve trunk; and a conductive lead capable of operatively connecting a waveform generator to one of the plurality of platinum nerve contact segments.

One embodiment is a method of increasing durability of a nerve cuff electrode by operatively connecting a plurality of segmented conductive contacts of the electrode with at least a single wire thus forming a segmented strip, the wire configured as helical portions separated by non-helical portions where the non-helical gap portions are secured to the surface of the conductive contacts. In this embodiment, the helical portions permit repeated electrode deformations, e.g., creases, wrinkles, and/or breaks, without breaking. The segmented conductive contacts result in decreased stress on contacts.

One embodiment is a method of using a segmented nerve cuff electrode to ameliorate sensory nerve pain in a patient in need thereof. In this embodiment, a waveform generator is operatively connected to the inventive electrode in contact with a trunk of a sensory peripheral nerve having a diameter exceeding 3 mm and up to 12 mm, e.g., a sciatic nerve or a tibial nerve. In use, the method prevents action potential transmission in the nerve upon application of a waveform of at least 5 kHz up to 50 kHz at one of a voltage ranging from 4 Vpp to 20 Vpp, or a current ranging from 4 mApp to 26 mApp at a plurality of contact surfaces with the nerve trunk for an interval sufficient to effect substantially immediate pain relief in the patient. The steps can be repeated as needed to ameliorate nerve pain. The electrode contacting the nerve can be mono-, bi-, or tri-polar. The electrode cuff inner diameter may range from about 5 mm to about 12 mm. The method may also be applied to an ilioinguinal nerve to ameliorate post-surgical hernia pain, to an intercostal nerve to ameliorate pain from shingles, to a sciatic nerve to ameliorate neuropathic diabetes pain, and to an occipital nerve to ameliorate migraine pain.

One embodiment is a method of using a segmented nerve cuff electrode to effect a desired response in a patient using the above-described method. The desired response may be ameliorating spasticity of a muscle enervated by the nerve, where the patient experiences spasticity amelioration substantially immediately upon application of the electrical waveform. The desired response may be ameliorating an urge to void the bladder and the patient experiences urge amelioration substantially immediately upon application of the electrical waveform, and the nerve contacted may be a pelvic nerve.

Successful results are disclosed from a method and apparatus that uses high frequency nerve block to acutely treat peripheral pain, either acute pain or chronic pain (more than 6 months in duration), in humans by blocking nerve conduction on an action potential. Acute treatment is defined as on demand treatment with substantially immediate pain relief effect. In one embodiment, the method is used in peripheral nerves having a diameter up to about 12 mm, i.e., in relatively large nerves such as the sciatic nerve. In one embodiment, the method is used on a nerve to ameliorate a non-pain condition by therapy to a nerve, e.g., motor nerves resulting in spasticity, e.g., nerves providing an urge to void in overactive bladder.

Previous therapy for pain of peripheral origin, e.g., damaged nerves in a limb, consisted of one or a combination of the following methods.

One previous therapy was local injection of a pharmacologic anesthetic such as lidocaine. The therapeutic effect often lasts only a short time, e.g., a few hours. Repeated dosing is typically not feasible because of toxicity of the anesthetic and other reasons.

Another previous therapy was conventional electrical stimulation by surface electrodes or surgically implanted electrodes (e.g., TENS, Peripheral Nerve and Spinal Cord Stimulator). Electrical stimulation therapy is used to treat back pain and joint pain, but produces inconsistent effects. The inconsistencies are due to the indirect nature of the therapy; instead of blocking pain signals from the origin of the pain, this type of electrical stimulation activates non-pain sensory nerves to generate other types of sensation (e.g., tingling) that mask the pain sensation. Such masking is by a complex, and often unreliable, interaction of various parts of the nervous system.

A potential therapy involves reversibly blocking peripheral nerves by applying high frequency alternating current directly on a nerve trunk. Specifically, a current ranging from 5 kHz to 50 kHz was applied; this was denoted as high frequency, compared to a current of less than 1 kHz applied in the conventional electrical stimulation described above. Efficacy of the high frequency alternating current therapy in acute non-human animal experiments (frog, cat) has been reported. U.S. Pat. Nos. 7,389,145 and 8,060,208 describe in general this electrical stimulation technology. No data are described.

One embodiment of the invention discloses a method for reversibly blocking an action potential in a peripheral nerve having a diameter exceeding 3 mm and up to about 12 mm, e.g., a sciatic nerve, a tibial nerve, etc., in a patient in need thereof. The method comprises providing an electrical waveform for an interval of time sufficient to effect substantially immediate pain relief, defined generally as within about 10 min. One embodiment uses a waveform ranging from 5 kHz to 50 kHz. One embodiment uses a 10 kHz sinusoidal waveform at a current ranging from 4 mApp to 26 mApp. The electrode can be retained in a cuff encircling the desired peripheral nerve in which the action potential is to be blocked; the cuff inner diameter may range from about 5 mm to about 12 mm. The time interval may be about 10 minutes, but an interval may be selected by a magnitude sufficient to effect pain relief in the patient. In one embodiment, the electrical waveform to effect pain relief ranges from a voltage from 4 Vpp to 20 Vpp, or a current ranging from 4 mApp to 26 mApp. The time of increasing magnitude can range from about 10 seconds to about 60 seconds with a steady ramp up of voltage or current. The waveform is provided by a waveform generator that is operatively connected to the electrode implanted in the patient; such methods are known in the art.

One embodiment is a device that reversibly blocks an action potential in a relatively large nerve, i.e., a nerve with a diameter exceeding about 3 mm and up to 12 mm. The apparatus has a self-curling sheet of non-conductive material that includes a first layer, which is pre-tensioned, and a second layer, which is not pre-tensioned. The two layers are configured to form a cuff containing or holding strips of conducive material therebetween. In embodiments, the device has one, two, three, four or more segmented strips of a conductive material that are disposed adjacent, but not transverse, to one longitudinally extending edge of the self-curling sheet, each of these strips of conductive material is connected to an electrically conductive lead. In one embodiment, the device contains one strip of a conductive material, termed a monopolar configuration. In one embodiment, the device contains at least two segmented strips, connected by an electrically conductive lead, of a conductive material, termed a bipolar configuration. In one embodiment, the device contains at least three segmented strips, connected by an electrically conductive lead, of a conductive material, termed a tripolar configuration. In one embodiment, the device contains at least four segmented strips, connected by an electrically conductive lead, of a conductive material. Multiple apertures, typically circular but not necessarily so limited in shape, are disposed at periodic intervals of the inner nerve-contacting surface along the curling length of one of the two non-conductive sheets or layers of the self-curling sheet/cuff. This provides contact to the nerve by exposing and providing continuous multiple conductive contact points. The exposure may be at any interval that exposes as much of the conductive material as possible or desirable, and exceeds the contact surface area of conventional electrodes. Each of the first or top non-conductive sheet or layer and the second or bottom non-conductive sheet or layer still retains and contains the conductive material therebetween, i.e., sandwiched inside the sheets or layers, so that the conductive material is in fact retained and does not pop out or come out while providing efficient current delivery. In one embodiment the non-conductive material is silicone, the electrically conductive lead is stainless steel, and the conductive material is platinum. Other materials for each of the non-conductive material, the electrically conductive lead or wire, and the conductive material are known in the art. In use, the device is operatively connected, e.g., by an external lead or wire, to a waveform generator that provides the regulated waveform.

One embodiment is a method for treating peripheral nerve pain in a patient in need of this treatment. The above-described device encircled a particular segment of a targeted peripheral nerve, e.g., a sciatic nerve, a tibial nerve. Using a patient-implanted electrode connected to an electrical waveform generator, an electrical waveform is applied for a time interval, e.g., 10 min, sufficient to effect substantially immediate patient pain relief, e.g., within 10 min, and an extended period of pain relief up to several hours. The current in one embodiment ranges from 4 mApp to 26 mApp, and in one embodiment ranges from 4 mApp to 26 mApp.

Implementation of electrical nerve block or activation in patients for pain management or other conditions often requires a direct interfacing device with peripheral nerves in the form of a cuff wrapping around a nerve trunk.

U.S. Pat. No. 8,731,676 discloses a bipolar nerve cuff electrode with two continuous platinum strips embedded in a silicone substrate used to wrap around a nerve trunk. However, breakage of the platinum strips was found where a larger nerve trunk and/or certain anatomical characteristics (such as short stumps in above-knee amputees) were encountered. Inspections of explanted electrodes revealed that the platinum strips situated around the nerve trunk were wrinkled/creased or broken along their length due to repeated bending when the nerve trunk was compressed and flattened during daily activities.

Realizing platinum is of low mechanical strength despite its superior biocompatibility and electrical characteristics for charge delivery, a design was conceptualized with multiple segmented platinum contacts and each segment connected with wires made of a durable and biocompatible conductive material, e.g., stainless steel (SS). The total surface area of all of the platinum contacts was equivalent to that of a continuous strip by increasing the width to compensate for the gaps between the contacts.

The configuration of the wire interconnection establishes the durability and flexibility of the cuff electrode. Specifically and in one embodiment, a 7-strand of 316LVM wire was wound into a helix. A gap was created along the helix wherever it overlaps with a platinum contact. Conventional spot welding was used for connecting the wire to the platinum contact. In embodiments, two wire helices lying in parallel were employed to provide redundancy. The helices were entirely embedded in the silicone sheeting and only the outer side of the platinum contacts was exposed to the surface of the nerve trunk.

Relative to prior electrodes, the inventive segmented nerve cuff electrode had extended durability under repeated compression. Enhanced durability was demonstrated by subjecting electrodes to repetitive cycles of compressions of up to 50% of original diameter followed by decompression to original diameter, and testing for continuity across segments. Cuffs incorporating continuous platinum strips underwent compression cycles on the order 1,000,000 cycles and remained intact.

In the inventive method, data from a human study using high frequency electrical nerve block technology for pain management are provided. In one embodiment, the result was that amputation pain was reduced. Application of 10 kHz alternating current generated by a custom generator via a custom implanted nerve electrode significantly reduced pain in the majority of patients treated by the method. The required voltage/current level is reported. The duration for achieving reliable pain relief in specific human nerves is reported. The required sequence and time to apply the electrical energy to minimize side effects is reported. The anticipated accompanying sensations and their time course is reported. The duration of pain relief after termination of the electrical current is reported. The cumulative effect of successive applications of the current on the extent of pain reduction is reported.

The apparatus was an implantable electrode operatively connected to an external or implanted waveform generator. The electrode was a spiral cuff electrode similar to that described in U.S. Pat. No. 4,602,624, more fully described below. In use, the electrode was implanted in a human mammal on a desired peripheral nerve trunk proximal to the pain source (e.g., a neuroma), such that the cuff encircled the desired peripheral nerve in which the action potential was to be blocked. The cuff inner diameter ranged from about 5 mm to about 12 mm. The sciatic nerve is known to have a relatively large nerve trunk; the diameter of the proximal part of the sciatic nerve in a human adult is about 12 mm. In one embodiment, the apparatus and method was used on the sciatic nerve to treat limb pain in above knee amputees. In one embodiment, the apparatus and method was used on the tibial nerve to treat limb pain in below knee amputees.

BRIEF DESCRIPTION OF THE DRAWINGS

FIG. 7A shows a general schematic of a tripolar electrode in an uncurled configuration.

FIG. 8 tabulates treatment outcomes from five patients.

Figure 1:
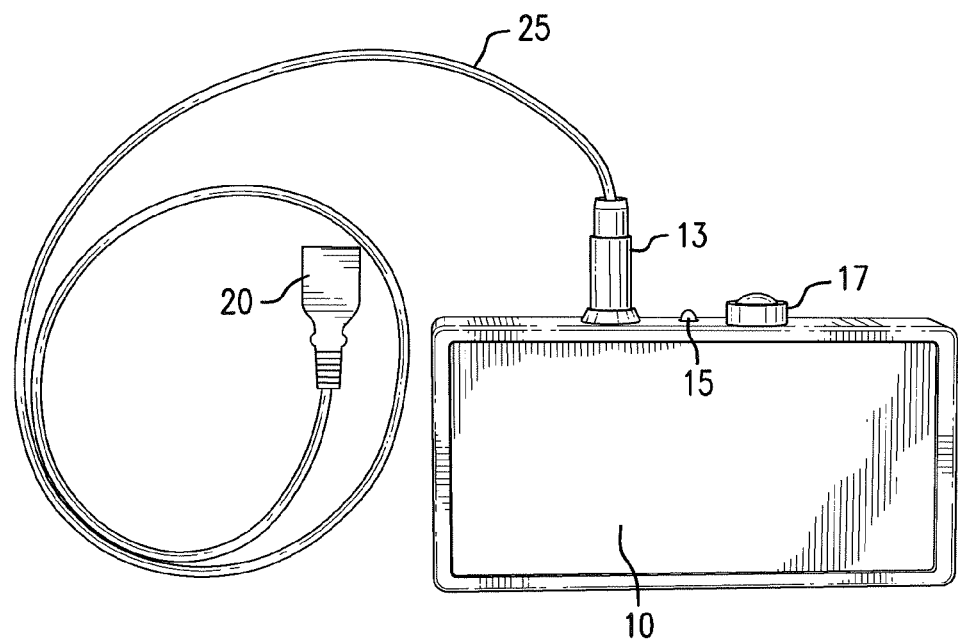
FIG. 1 is a perspective view of an external waveform generator and interconnection cable.
Figure 2:
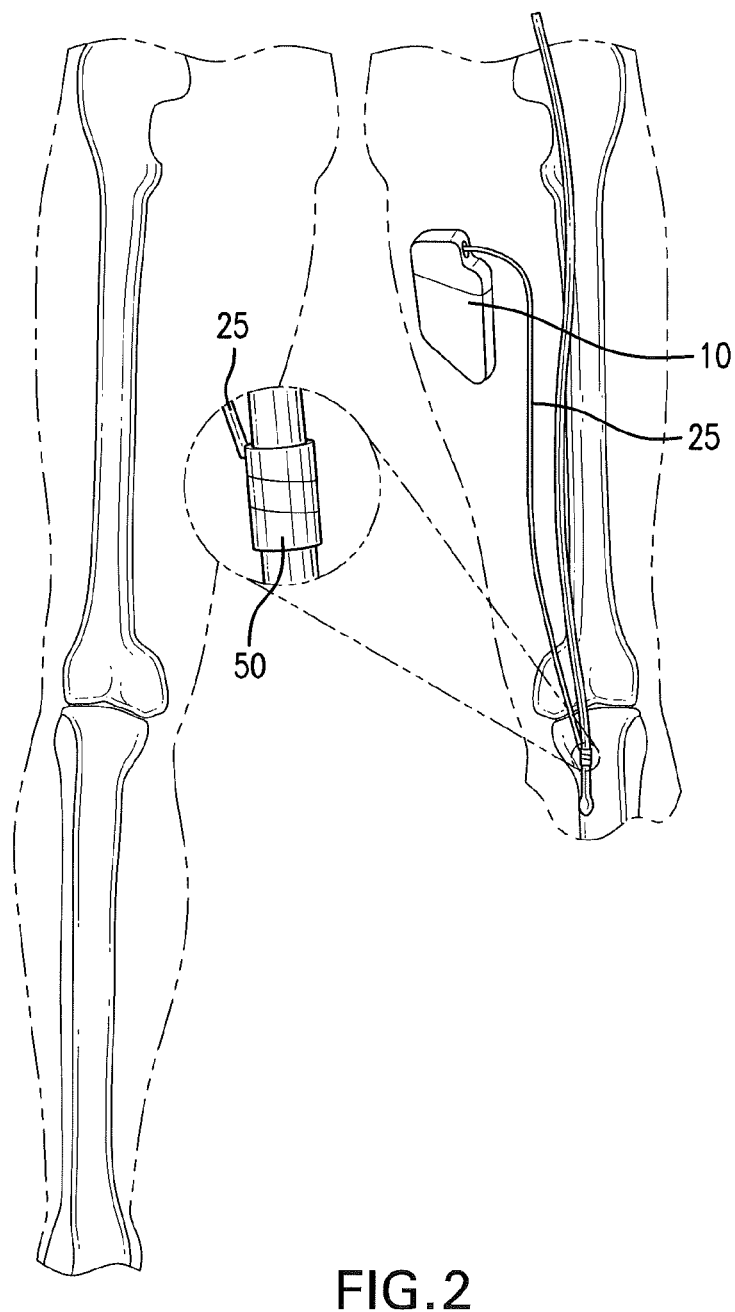
FIG. 2 shows an in-use implanted waveform generator operably connected to a nerve cuff electrode encircling a patient's nerve.

In use, the external and implanted waveform generator, shown in FIGS. 1 and 2 respectively, delivered high frequency alternating current in any form (sinusoidal wave, rectangular, other shape) sufficient to block the nerve action potential. In use, the operator selectively regulated the amount of current applied to the electrode, the duration, and any other desired parameters (e.g., continuous versus intermittent), etc. for therapy. In one embodiment, a sinusoidal waveform frequency of 10 kHz effectively and repeatedly reduced pain. In one embodiment, a sinusoidal waveform frequency ranging from 20 kHz to 30 kHz effectively reduced pain, but required about two times higher voltage and higher current for a 20 kHz sinusoidal waveform, and about three times higher voltage and higher current for a 30 kHz sinusoidal waveform, compared to that required for a 10 kHz sinusoidal waveform.

Using a sinusoidal waveform frequency of 10 kHz, patients reported a sensation threshold at a voltage ranging from 1 Vpp to 10 Vpp, and at a current ranging from 1 mApp to 16 mApp. The sensation threshold was the minimum stimulation at which a patient indicated that s/he feels a sensation due to the applied current, e.g., a patient may feel a tingling sensation.

Indication of a sensation threshold does not indicate pain relief, which is defined broadly as any pain mitigation or amelioration including but not limited to complete pain relief. Using a sinusoidal waveform of 10 kHz, the patient's relief from pain was achieved at a voltage ranging from 4 Vpp to 20 Vpp, and at a current ranging from 4 mApp to 26 mApp. The interval between the two parameters (the voltage/current required to be applied to achieve a sensation threshold, versus the voltage/current required to be applied to achieve pain relief) was optimally achieved by a conservative steady ramping up over a range from about 10 seconds to about 60 seconds. This minimized or prevented the patient from experiencing pain or other undesirable sensations at the outset of therapy.

Figure 3B:
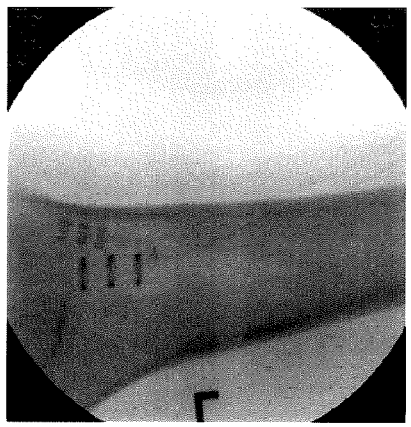
FIGS. 3A, 3B are a photograph on the implanted cuff and electrode, and a confirmatory fluoroscopy image of same, respectively.
Figure 3A:
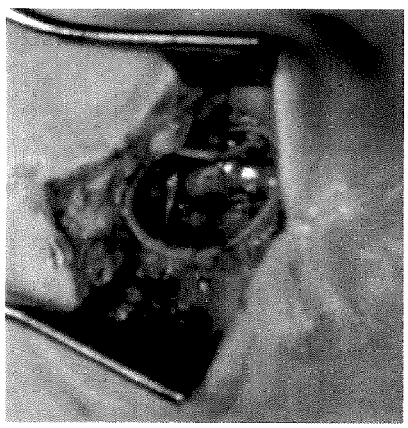

In one embodiment, the electrode was implanted on the tibial nerve, as shown in FIG. 3A. Proper implantation was verified by fluoroscopy visualization, as shown in FIG. 3B.

In one of five patients experiencing pain post lower-limb amputation, the extent of baseline pain intensity and relief of this pain by a self-administered narcotic pill were compared to the extent of each of baseline pain intensity and relief of this pain using the disclosed nerve block apparatus and method was self-assessed over a 21 consecutive day period. The patient self-assessed pain intensity using a 0-10 scale where 0 is no pain and 10 is as bad as it could be. The narcotic was hydrocodone/APAP formulated as a tablet at a dose of 10 mg/325 mg. The patient self-administered the tablet orally as needed.

When self-administering the electrical nerve block therapy, the parameters over which the patient did not have control were the amount of current applied, and the duration of each administration period. The parameters over which the patient did have control were the time(s) during the 24 hour period to self-administer the therapy, and the time interval between the administrations. In one embodiment, each treatment was for 10 minutes. In one embodiment, one self-administered electrical treatment for 10 minutes was immediately followed by at least one additional self-administered electrical treatment for 10 minutes to result in cumulative pain reduction effect. The amount of current/voltage applied during each interval ranged from 4 mApp to 26 mApp/4 Vpp to 20 Vpp, respectively.

Figure 5:
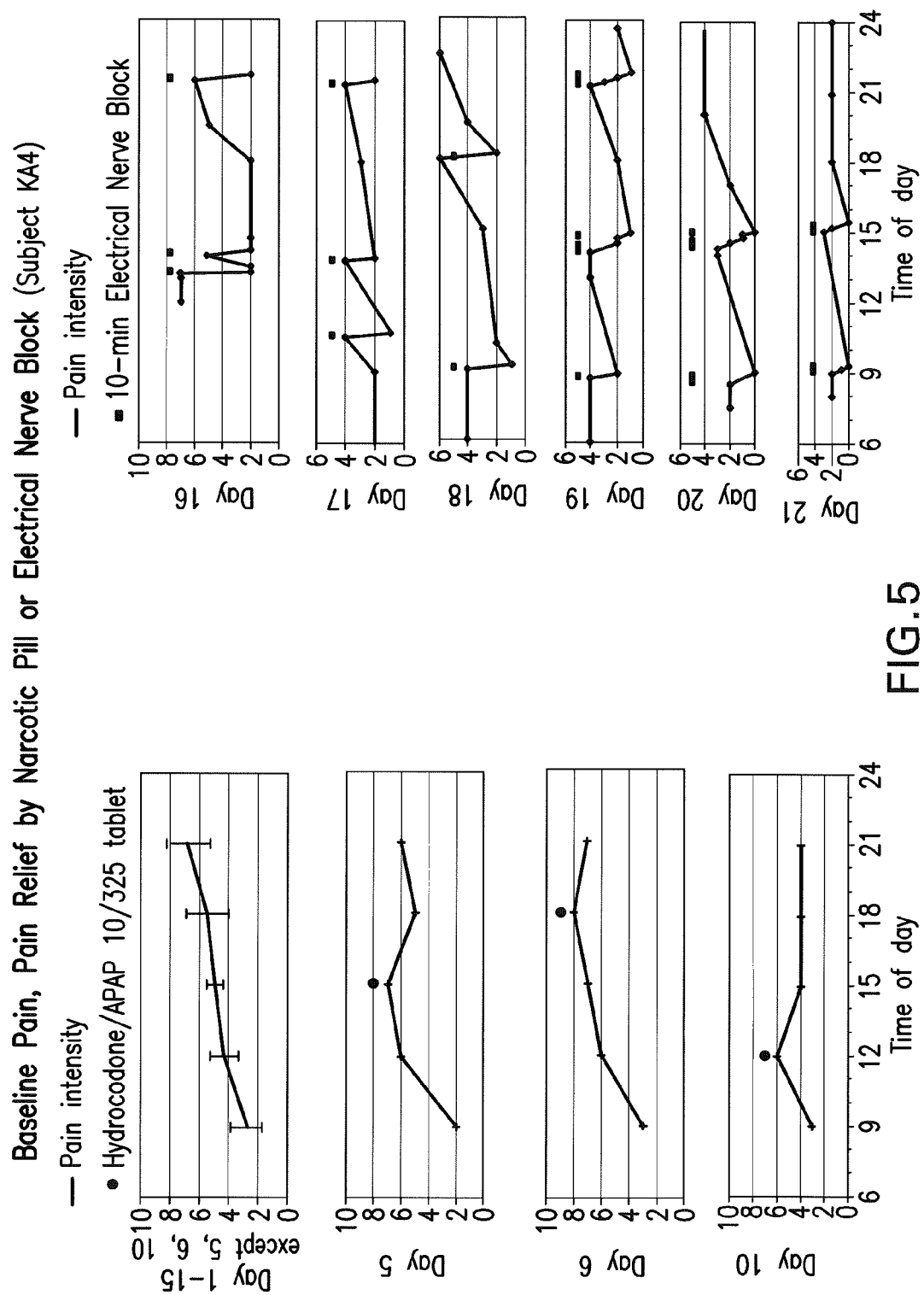
FIG. 5 graphs one patient's pain relief comparing use of the invention versus drug treatment.
Figure 6:
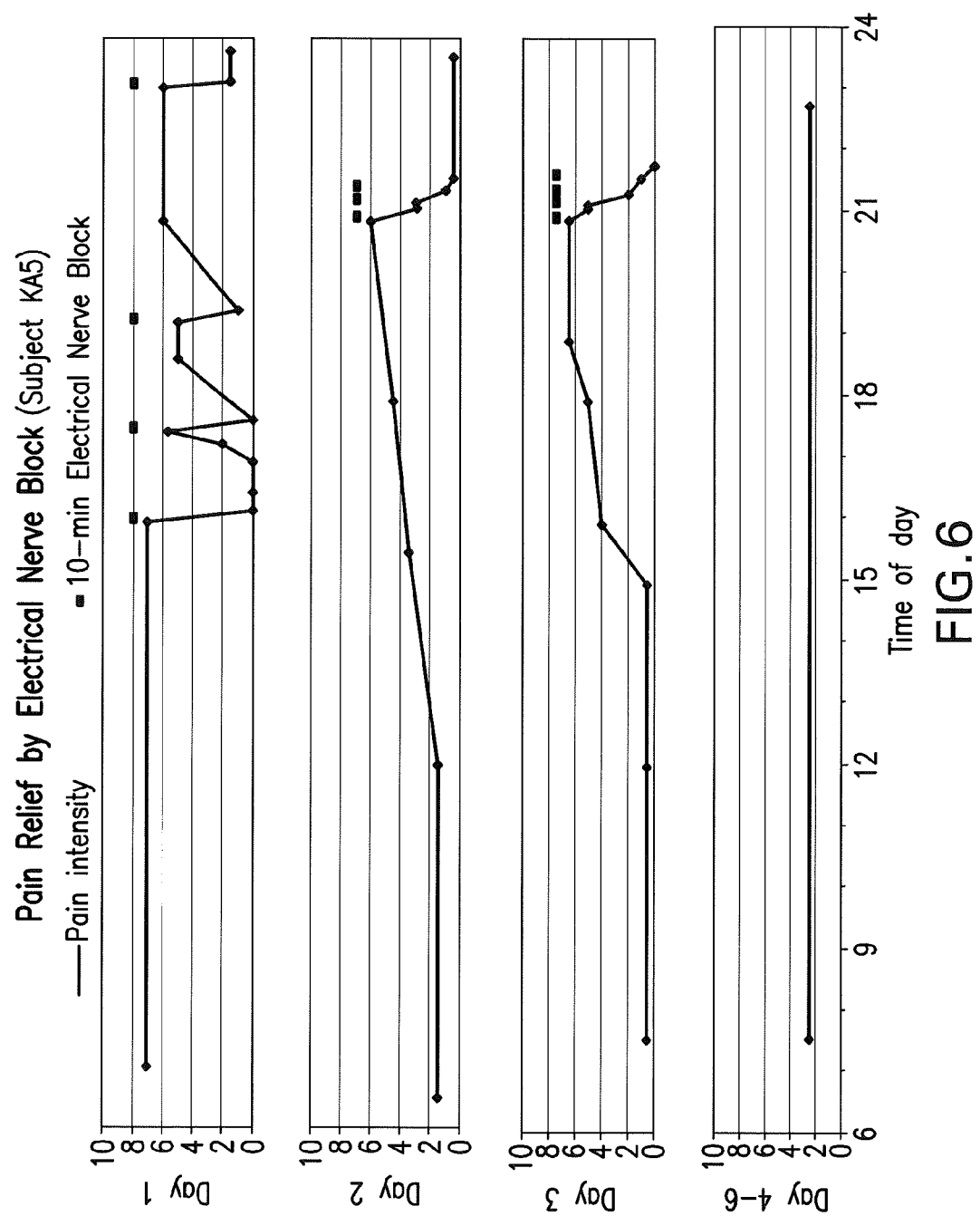
FIG. 6 graphs one patient's pain intensity and pain relief using the invention.

Specific selected data for each of two patients are shown in FIGS. 5 and 6 respectively. A summary of the results for all of the five patients is shown in FIG. 8.

The patients reported that they experienced pain mitigation within minutes of treatment onset. The patients reported that sensations such numbness, tingling, and pulling, subsided within minutes after treatment onset. The patients reported that, after a 10 min treatment (application of electrical blocking current), they experienced pain reduction that was sustained up to several hours after cessation of treatment.

A description of various embodiments of the electrode used for nerve conduction block is as follows. They differ from the use of the apparatus disclosed in Naples U.S. Pat. No. 4,602,624. Naples' electrode is used to stimulate, i.e., excite, activate, generate, an action potential in a nerve having a diameter of about 1 mm to about 3 mm. In Naples, four sets of rectangular-shaped electrodes constitute the contact points that are sandwiched between two layers of a non-conductive material such as silicone. The layers of non-conductive material were self-curling. The conductive contact points were disposed at uniform intervals therebetween at sites on the inner circumference of a first resiliently extensible layer. The conductive contact points are connected by conductive wires or leads, e.g., stainless steel wires. The layers have openings (windows) in the non-conductive material to expose the conductive contact points to the nerve upon selective regulation, in this case, activation to initiate an action potential. The distance between the openings (separation distance) and curling length of the layers is proportional to the nerve diameter.

In attempting to block an action potential in nerves having a diameter exceeding about 3 mm, the previously described apparatus and method is inadequate. This is because a simple scale-up of the aforementioned design did not permit adequate current flow that is necessary to block conduction of an action potential in a nerve that has a relatively larger diameter as compared to a typical nerve which has a diameter that does not exceed about 3 mm. For example, the sciatic nerve in an adult human has a diameter exceeding about 3 mm; it can be up to 12 mm diameter. The sciatic nerve is a frequent source of pathology and often requires therapy. The inventive method was used on nerves having a diameter exceeding about 3 mm for nerve conduction block.

In one embodiment the inventive method was used on nerves having a diameter between about 1 mm and about 8 mm. In one embodiment the inventive method was used on nerves having a diameter between about 3 mm and about 10 mm. In one embodiment the inventive method was used on nerves having a diameter between about 8 mm and about 12 mm. In one embodiment the inventive method was used on nerves having a diameter up to about 12 mm. The inventive method blocked an action potential in a nerve, including the sciatic nerve, and thus ameliorated and/or mitigated peripheral nerve pain. The inventive method was not used to generate an action potential in a nerve; rather, it was used to block conduction of an action potential. Blocking conduction of an action potential in a nerve, versus stimulating an action potential in a nerve, requires higher current, and hence lower resistance, at the interface between the nerve and the electrode. The inventive method used a generator that advantageously provided adequate voltage with lower power consumption. The inventive method thus minimized thermal damage to tissue from heat that was generated during its use, while providing improved efficiency.

In all embodiments, the electrode had a relatively larger contact surface with the nerve than conventional electrodes, such as Naples' electrode. As only one illustrative example used in the inventive method, the apertures were spaced at an interval ranging from 0.5 mm up to 1.9 mm. In one embodiment, the apertures were spaced at 1.0 mm intervals, defined as a center-to-center dimension between neighboring apertures.

Figure 4:
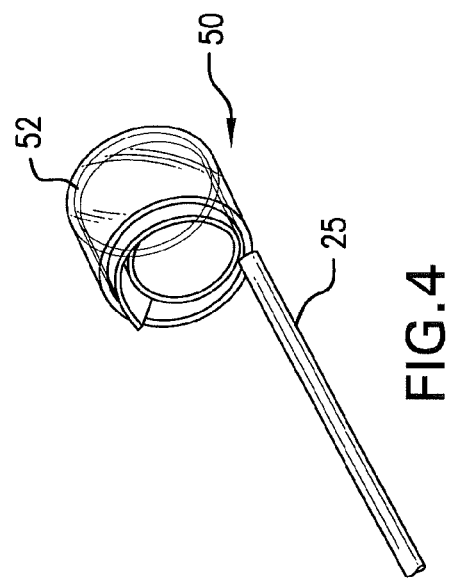
FIG. 4 schematically shows the nerve cuff electrode and lead.
Figure 7B:
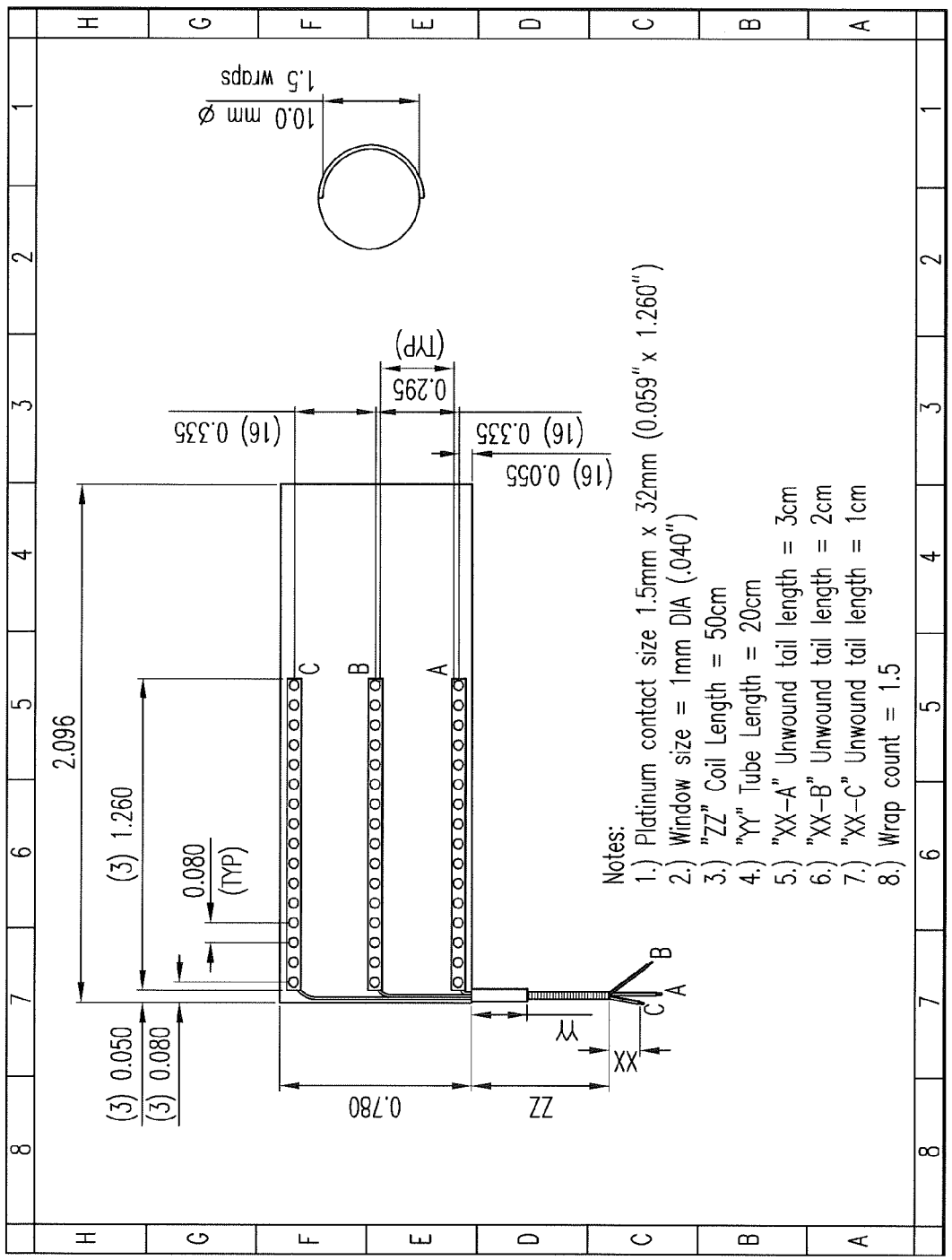
FIG. 7B shows one embodiment of FIG. 7A with specific dimensions.

As shown in FIG. 1, an external waveform generator 10 had an electrode connector 20 operatively connected with cable 25, having connector 13, LED indicator 15, and on/off indicator 17. As shown in use in FIGS. 2, 3, and 4, nerve cuff electrode 50 had conductive material 51 contained in self-curling sheet 53 and lead 25 to connect to the waveform generator 10. As best shown in FIGS. 7A, 7B, the conductive material 51 was both contained and retained within an implantable expandable spiral cuff 52, shown in FIG. 4. The cuff 52 provided the flexibility required for use to contact and regulate nerves having a diameter exceeding about 3 mm and up to about 12 mm, and provided a non-rigid contact surface with the nerve in order to minimize tissue damage.

In one embodiment, shown in general FIG. 7A and in one specific embodiment shown in FIG. 7B, the electrode contained continuous strips of conductive material 51, specifically platinum in FIG. 7B, in a sandwich configuration, with two opposing surfaces or sheets of a non-conductive material 53, specifically silicone in FIG. 7B, along the entire length of the non-conductive material 51. The non-conductive material 53 was self-curling. To provide points of contact of conductive material 51 with the nerve, around which the cuff 52 was implanted, openings or apertures 57 were created in one surface of the non-conductive material 53 at periodic intervals 59. The spacing of the intervals 59 is such that the conductive material 51 was contained and retained within the non-conductive material 53 during use, i.e., the non-conductive material does not pop out or come out, and provides sufficient exposure of the conductive material 51 for electrical contact with the nerve. In one embodiment, the openings 57 were created at 1 mm intervals. In one embodiment, the openings 57 were created at intervals ranging between about 1 mm to about less than 2 mm. The openings 57 were created in the non-conductive material 53; it was at these openings 57 that the nerve was exposed to the conductive material 51 in order to block conduction of an action potential. In a bi- or tri-polar embodiments, the distance or spacing between strips is 1:1 depending upon the nerve size to be treated; larger sized nerves can accommodate larger space between the strips. In FIG. 7A, for each electrode, the strip length with conductive material contacts 70 is shown for each of leads or wires A, B, and C. This electrode design achieved efficient current delivery to effect this blockage of the action potential. This electrode design contained and retained the conductive material 51 within the two layers of non-conductive material 53.

Figure 9:
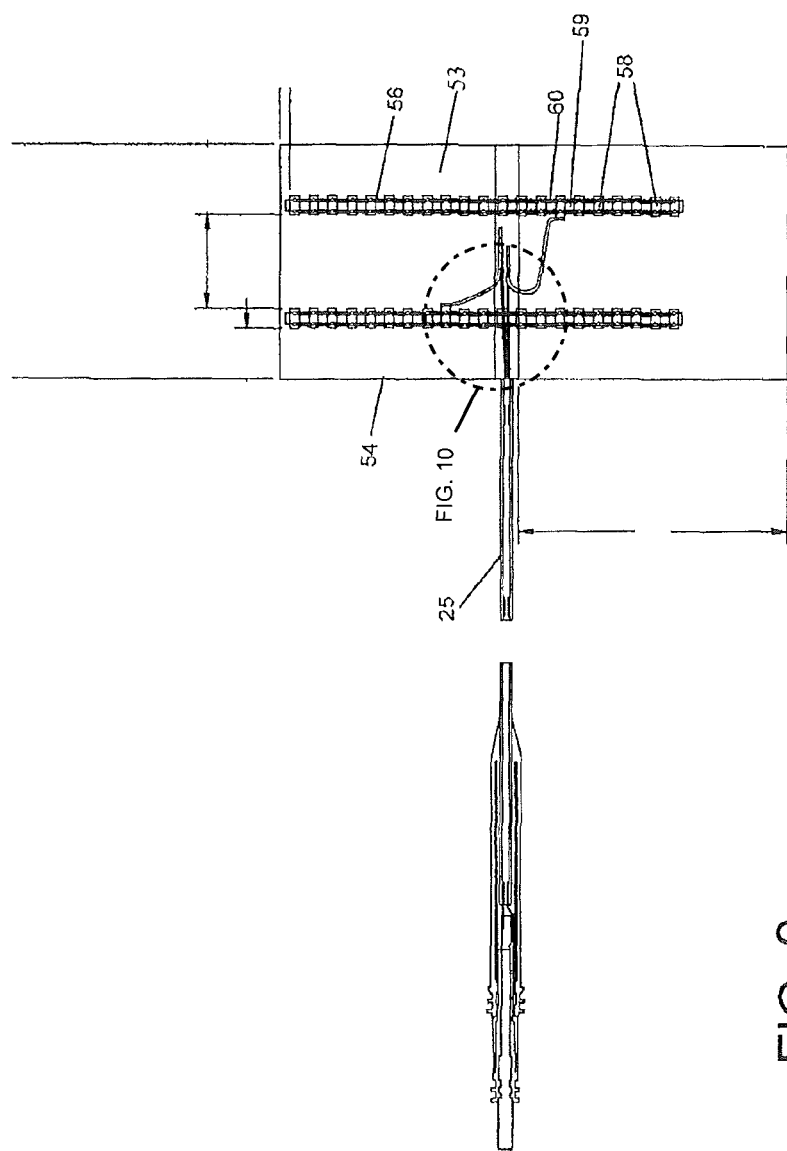
FIG. 9 shows a schematic of a lead and a nerve cuff electrode in an uncurled configuration incorporating a segmented contact strip and lead.
Figure 10:
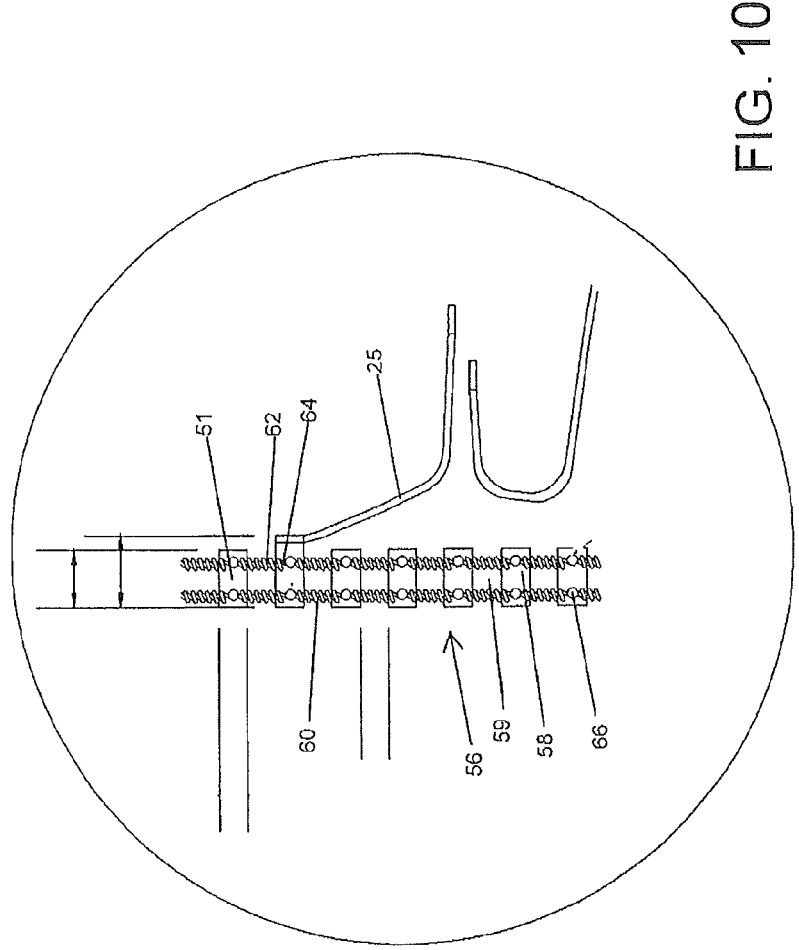
FIG. 10 shows a detailed schematic view of a segmented contact strip.

In one embodiment, shown in general in FIGS. 9 and 10, the lead 25 was operatively connected to a self-curling nerve cuff 54 with a segmented strip 56 of conductive material 51, such as platinum. Each segmented strip 56 was formed of a plurality of contact segments 58 operatively connected by wire 60, made of a durable and conductive biocompatible material such as stainless steel (SS), to form a generally linear string of the contact segments 58. The total surface area of all of the contact segments 58 may be equivalent to that of a continuous contact strip by increasing the width of the segments 58 to compensate for the spaces 59 therebetween.

Such wire 60 was wound into a helix 62, with gaps 64 therein to accommodate attachment to the contact segments 58 by conventional spot welds 66. In one embodiment, the stainless steel wire is 7-strand 316LVM wire. The helical structure of the wire 60 improves durability and flexibility of the cuff electrode by enhancing the ability of segmented strip 56 to curl about the nerve trunk in cooperation with the nerve cuff 54 by allowing the segmented strip 56 to wrap about the nerve trunk by the wire 60 without significantly bending, wrinkling, or creasing the contact segments 58 themselves. The helical structure of the wire 60 is well-suited to absorb stresses introduced by conformational changes of the nerve trunk as the patient conducts daily activities, because the helixes 62 of the wire 60 can bend and axially expand or compress in response to such environmental changes without impacting the contact segments 58 themselves.

In one embodiment, two parallel wires 60 were used to connect the contact segments 58 to provide redundancy in case one wire failed. The helixes 62 are entirely embedded in non-conductive material 53, such as silicone sheeting, such that only the side of the contact segments 58 opposite the helixes 62 is exposed to the surface of the nerve trunk.

In the embodiments shown in FIGS. 9 and 10, the nerve cuff 54 includes two segmented strips 56 of conductive material 51 disposed adjacent, but not transverse, to one longitudinally extending edge of the self-curling sheet, where each of these strips 56 is connected to the electrically conductive lead 25 (a bipolar configuration). However, the nerve cuff 54 may alternately contain only one segmented strip 56 (monopolar), or three (tripolar), four, or more segmented strips 56 as suitable for the particular application.

Although the disclosed segmented strips are described in the context of reversibly blocking an action potential in large human nerve trunks, the utility of the disclosed segmented strips 56 is broadly applicable to other nerve stimulation and/or blocking contexts, as well as to a variety of other applications where it is desirable to wrap an electric contact surface about an outer surface of a target substrate, e.g., for contact with a large nerve trunk for restoring motor or sensory function. The dimensions of the segmented strips 56, wire(s) 60, and other components are scalable.

Figure 11A:
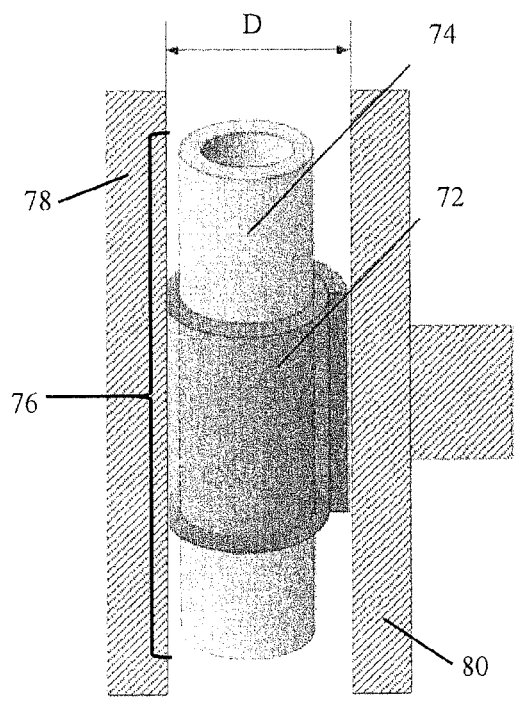
FIGS. 11A and 11B show schematic views of an apparatus to assess durability of a nerve cuff electrode.
Figure 11B:
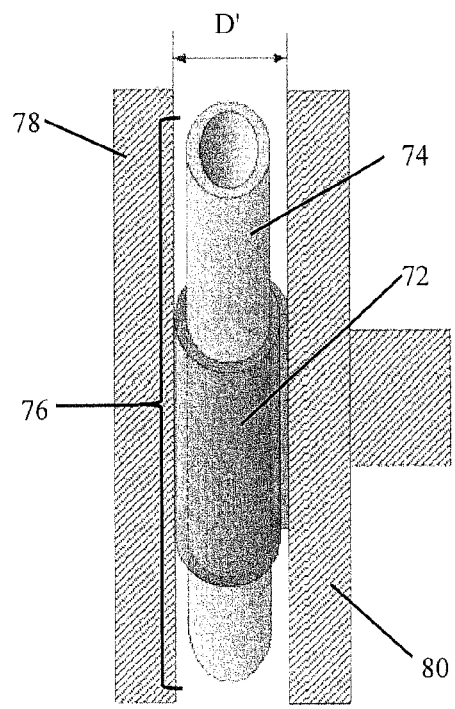

Durability for one embodiment of the inventive electrode with segmented strips 56 was assessed compared to durability of an electrode with continuous strips. The electrode with segmented strips 56 included a conductive band of segmented platinum contacts connected by a stainless steel helix. The electrode with continuous strips included a conductive band of a continuous platinum strip. In each case, the respective cuff 72 was wrapped around a length of flexible rubber tubing 74 of 3 mm to 12 mm diameter, serving as a surrogate nerve trunk to form a cuff-tube assembly 76 (FIGS. 11A-B). The cuff-tube assembly 76 was mounted between two parallel plates 78, 80 configured to move relative to each other to compress and decompress the assembly 76.

For each assessment, the cuff-tube assembly 76 was repeatedly compressed and decompressed between the plates 78, 80 between an uncompressed state (FIG. 11A), where assembly 76 has diameter D, and a compressed state (FIG. 11B), where assembly 76 has compressed diameter D'). The cuff-tube assembly 76 was compressed by 30%-50%, i.e., at 30% compression, D'=0.7×D, and at 50% compression, D'=0.5×D. Compressions were performed at 200 cycles per minute. During these assessments, the cuff-tube assembly 76 was mounted at different orientations about the longitudinal axis of the assembly 76 to test the durability of the cuff 72 under stress from various directions. The electrical continuity of the conducting band within the cuff 72 was continuously monitored by a data acquisition system.

The cuff with continuous strips failed, i.e. electrical continuity was disrupted, after an average of 143,667 cycles at 30% compression, and after 16,000 cycles at 50% compression. In contrast, the cuff with segmented strips failed, in two cases, after 5,500,000 and 3,590,000 cycles at 50% compression, and in another case after ~4,600,000 cycles including 1.40 million cycles at 30% compression and 3.18 million cycles at 50% compression. In other cases, testing terminated without failure after several million cycles at 50% compression. Consider Table 1, below:

| Item Number | Cuff Type | Compression Ratio | Cycles to Failure |
|---|---|---|---|
| 1 | Continuous | 30% | 138,000 |
| 2 | Continuous | 30% | 63,000 |
| 3 | Continuous | 30% | 230,000 |
| 4 | Continuous | 50% | 16,000 |
| 5 | Segmented | 30% for 1.40M 50% for 3.18M | 4,600,000 |
| 6 | Segmented | 50% | 5,500,000 |
| 7 | Segmented | 30% for 1.19M 50% for 3.68M | >5,100,000* |
| 8 | Segmented | 50% | >3,400,000* |
| 9 | Segmented | 50% | >3,400,000* |
| 10 | Segmented | 50% | >3,700,000* |
| 11 | Segmented | 50% | >3,700,000* |
| 12 | Segmented | 50% | 3,590,000 |
| 13 | Segmented | 50% | >4,030,000* |
| 14 | Segmented | 50% | >4,030,000* |

*Test terminated before failure

These testing data demonstrated that the cuff with segmented strips is at least twenty-five times more durable than the cuff with continuous strips. Cuffs with continuous strips, currently used in clinical practice, typically show breakage in clinical applications as early as six months after implantation. Patients thus must regularly seek further professional care to replace damaged cuffs. Thus, the disclosed cuff with segmented strips significantly increases the useful life of devices into which it is incorporated, thereby decreasing the procedures, cost, and inconvenience to patients having such implanted devices.

In one embodiment, the curled configuration of the apparatus had a diameter of 10 mm with a 1.5 wrap, meaning that one half of the circumference contained a single sandwiched sheet (i.e., 2 layers) of non-conductive material 53, and the other 1.5 wrap of the circumference contained two sandwiched sheets (i.e., 4 layers) of non-conductive material 53. Any wrap resulting in a compliant, flexible cuff that does not damage the nerve may be used. The interpolar distance was about 0.75 times to 1.5 times the inner cuff diameter. The contact surface area was relatively larger than the contact surface area of conventional electrodes, such as the electrode Naples disclosed for nerve stimulation and activation, safely delivered the required higher amount of charge to block the nerve action potential, even in nerves up to 12 mm in diameter.

In one embodiment, the electrode was bipolar. In another embodiment, the electrode used three contact groups, i.e., tripolar. In this embodiment, the electrode contained three continuous strips of conductive material, connected by electrically conductive leads (A, B, C in FIGS. 7A, 7B), that was provided between the two opposing non-conductive surfaces in the same manner as described above for two continuous strips of conductive material. The separation, i.e., distance, between the two, three, or more conductor bands is a function of the diameter of the cuff. The ratio of separation: diameter ranged between 0.75:1.5.

The above-described electrode blocked numerous nerve fascicles and/or nerve fibers. The blockage was reversible; the cuff was implantable along any length of nerve at any site, and electrical parameters (current, voltage, duration, etc.) were selected by the operator. In one embodiment, the recipient of the implantable apparatus is the operator. In one embodiment, a health care professional is the operator. Use of the electrode results in lower resistance at the interface between the nerve and the electrode. Such multiple points of contact, and relatively large openings, enables the electrode to block at least one portion of the nerve trunk. In the embodiment with a tripolar configuration, the electrode can be used to first block at least one portion of the nerve trunk, and then stimulate the other portion to verify blockage.

The inventive method has use in a variety of pain and non-pain applications. One embodiment uses the method and electrode to block peripheral nerve pain. Besides use to ameliorate amputation pain, the uses and description of which was previously described, other examples of ameliorating pain include, but are not limited to, ameliorating neuropathic pain, nociceptive pain, chronic neurogenic pain, migraine pain, post-herpetic neuralgia, pelvic pain, chronic post-surgical pain, post-surgical pain, and neuralgia. As known in the art, pain is defined as an unpleasant sensation caused by noxious stimulation of the sensory nerve endings. Amputation pain is pain resulting from the surgical removal of a part of the body or a limb or a part of a limb to treat for therapy resulting from, e.g., pathology, trauma, etc. Neuropathic pain is pain that results from the direct inputs of nervous tissue of the peripheral or central nervous system, generally felt as burning or tingling and often occurring in an area of sensory loss. Nociceptive pain is pain that results from stimulation of the neural receptors for painful stimuli, i.e., inputs of nociceptors. Chronic neurogenic pain is pain that originates in the nervous system and persists over time (i.e., not acute but chronic). Migraine pain result in headaches and is related to dilation of extracranial blood vessels, the origin of which may be defined (e.g., consumption of certain foods, external stimuli) or may be unknown. Post-herpetic neuralgia is a form of neuralgia with intractable pain that develops at the site of a previous eruption of herpes zoster. Pelvic pain is pain that is centered in the pelvis region i.e. lower part of the trunk of the body. Chronic post-surgical pain is pain persisting for a long period of time beginning after treatment of disease or trauma by manipulative and operative methods. Post-surgical pain is pain beginning after treatment of disease or trauma by manipulative and operative methods. Neuralgia is pain, often severe and characterized as "stabbing", resulting from any number of nervous system pathologies or disorders.

In other embodiments, the inventive method is used in non-pain applications where blocking the action potential of a nerve provides the desired amelioration outcome. One example of such a non-pain use is in ameliorating obesity. As known in the art, obesity is an abnormal increase in the proportion of fat cells, mainly in the viscera and subcutaneous tissues. The inventive method may be used on the vagus nerve in this embodiment. Another example of such a non-pain use is in ameliorating overactive bladder, which is a colloquial term for bladder storage function disorders or pathologies. The method and electrode can be used on the pelvic nerve to ameliorate the sudden urge to void that may be difficult to suppress and may lead to incontinence. Another example of such a non-pain use is in ameliorating spasticity of any motor nerve; spasticity results in excessive muscle contraction and can be due to any of several nervous system disorders. The following hypothetical examples illustrate these embodiments.

A patient with advanced type 2 diabetes is experiencing neuropathic pain in his feet as a result of loss of blood flow to his legs. Normal doses of pain-killing narcotics are either ineffective or cause undesirable side effects. After implantation of the electrode and placement of the cuff on the right sciatic nerve trunk at the popliteal fossa, the patient self-treats pain for 10 minutes at 10 mApp, experiencing immediate pain relief. The patient repeats the procedure on demand, as needed.

A migraine patient experiences severe headaches unresponsive to conventional treatment. After implantation of the electrode and placement of the cuff on the greater occipital nerve trunk, the patient self-treats pain for 10 minutes at 10 mApp, experiencing immediate pain relief. The patient repeats the procedure on demand, as needed.

A patient with shingles experiences postherpetic neuralgia, unresponsive to conventional treatment. After implantation of the electrode and placement of the cuff on the intercostal nerves, the patient self-treats pain for 10 minutes at 10 mApp, experiencing immediate pain relief. The patient repeats the procedure on demand, as needed.

A post-operative inguinal hernia repair patient experiences chronic pain. After implantation of the electrode and placement of the cuff on the ilioinguinal nerve, the patient self-treats pain for 10 minutes at 10 mApp, experiencing immediate pain relief. The patient repeats the procedure on demand, as needed.

A patient with overactive bladder syndrome undergoes a procedure for implantation of the electrode and placement of the cuff on the pelvic nerve. The patient self-treats at 10 mApp upon an urge to urinate, experiencing urge cessation.

A patient with muscle spasticity undergoes a procedure for implantation of the electrode and placement of the cuff on a motor nerve. The patient self-treats at 10 mApp when needed, ameliorating spasticity of the muscle to which the nerve innervates The embodiments shown and described are specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A nerve cuff electrode comprising
   a plurality of conductive nerve contact segments, the plurality of segments having an inner surface configured to contact a nerve trunk and an outer surface configured not to contact the nerve trunk;
   at least a single wire of a conductive biocompatible material operatively connecting the plurality of conductive nerve contact segments thus forming a segmented strip, the at least a single wire configured as helical portions separated by non-helical portions where the non-helical portions are secured to the outer surface of the conductive nerve contact segments, the helical portions configured to bend and axially expand or compress in response to stress induced by conformal changes when the nerve cuff electrode is implanted in a patient; and a conductive lead capable of operatively connecting a waveform generator to at least one of the plurality of nerve contact segments.

2. The nerve cuff electrode of claim 1 where the helical portions of the at least a single wire are along a wire length between the conductive nerve contact segments.

3. The nerve cuff electrode of claim 1 where the non-helical portions of the at least a single wire are secured to the conductive nerve contact segments by a plurality of spot welds.

4. The nerve cuff electrode of claim 1 where the helical portions of the at least a single wire are embedded in a non-conductive material.

5. The nerve cuff electrode of claim 4 where the non-conductive material is silicone.

6. The nerve cuff electrode of claim 1 where the non-helical portions of the at least a single wire connect the conductive nerve contact segments.

7. The nerve cuff electrode of claim 1 further comprising a second wire of the at least a single wire operatively connecting the plurality of nerve contact segments, the second wire generally parallel with a first wire of the at least a single wire.

8. The nerve cuff electrode of claim 1 where the conductive nerve contact segments are platinum.

9. The nerve cuff electrode of claim 1 where the wires are stainless steel.

10. The nerve cuff electrode of claim 1 in which the at least a single wire is disposed adjacent to one longitudinally extending edge of the nerve cuff electrode.

11. The nerve cuff electrode of claim 1 wherein the nerve cuff electrode is embedded in a non-conductive nerve cuff.

12. The nerve cuff electrode of claim 11 wherein the nerve cuff electrode includes multiple segmented strips embedded in the non-conductive nerve cuff.

13. The nerve cuff electrode of claim 11 wherein the nerve cuff electrode includes only one segmented strip embedded in the non-conductive nerve cuff.

14. A nerve cuff electrode comprising:
a plurality of platinum nerve contact segments, each nerve contact segment comprising an inner surface configured to contact a nerve trunk and an outer surface configured not to contact the nerve trunk;
at least two wires of a conductive biocompatible material operatively connecting the plurality of platinum nerve contact segments thus forming a segmented strip, the at least two wires configured as helical portions separated by non-helical portions where the non-helical portions connect to the outer surface of the plurality of platinum nerve contact segments not contacting the nerve trunk by a plurality of resistive welds, the at leat two wires embedded in a silicone sheet such that only the inner surface of the plurality of platinum nerve contact segments contacts the nerve trunk, the helical portions configured to bend and axially expand or compress in response to stress induced by conformal changes when the nerve cuff electrode is implanted in a patient; and
a conductive lead capable of operatively connecting a waveform generator to one of the plurality of platinum nerve contact segments.

15. A method of using a segmented nerve cuff electrode to ameliorate sensory nerve pain in a patient in need thereof, the method comprising:
(a) connecting a waveform generator operatively to the nerve cuff electrode of claim 1 implanted in a patient and contacting a trunk of a sensory peripheral nerve having a diameter exceeding 3 mm and up to 12 mm in the patient, resulting in prevention of action potential transmission in the sensory peripheral nerve upon application of a waveform of at least 5 kHz up to 50 kHz at one of a voltage ranging from 4 Vpp to 20 Vpp, or a current ranging from 4 mApp to 26 mApp at a plurality of contact surfaces with the nerve trunk for an interval sufficient to effect substantially immediate pain relief in the patient, and
(b) optionally repeating step (a) as needed to ameliorate nerve pain.

16. The method of claim 15 where the sensory peripheral nerve is selected from the group consisting of a sciatic nerve, a tibial nerve, and combinations thereof.

17. The method of claim 15 where step (a) uses a mono-, bi-, or tri-polar electrode contacting the sensory peripheral nerve.

18. The method of claim 15 where the nerve cuff electrode has an inner diameter ranging from about 5 mm to about 12 mm.

19. The method of claim 15 where the nerve cuff electrode has a relatively larger contact surface with the sensory peripheral nerve than conventional electrodes.

20. A method for reversibly blocking an action potential in a sensory nerve of a patient to effect a desired response in the patient, the method comprising
(a) connecting a waveform generator operatively to the nerve cuff electrode of claim 1 implanted in a patient and contacting a trunk of the sensory nerve in the patient, resulting in prevention of action potential transmission in the sensory nerve upon application of a waveform of at least 5 kHz up to 50 kHz at one of a voltage ranging from 4 Vpp to 20 Vpp, or a current ranging from 4 mApp to 26 mApp, to the nerve trunk for an interval sufficient to effect a substantially immediate response in the patient, and
(b) optionally repeating step (a).

21. The method of claim 20 where the desired response is ameliorating spasticity of a muscle enervated by the sensory nerve and the patient experiences spasticity amelioration substantially immediately upon application of the waveform.

22. The method of claim 20 where the desired response is ameliorating an urge to void a bladder and the patient experiences urge amelioration substantially immediately upon application of the waveform.

23. A method of ameliorating sensory nerve pain in a patient in need thereof, the method comprising
(a) connecting a waveform generator operatively to the electrode of claim 1 implanted in the patient to contact a trunk of a sensory peripheral nerve in the patient, the method resulting in prevention of action potential transmission in the sensory peripheral nerve upon application of a waveform of at least 5 kHz up to 50 kHz where the frequency blocks but does not stimulate and is not used to generate an action potential in a nerve but rather to block conduction of an action potential at one of a voltage ranging from 4 Vpp to 20 Vpp, or a current ranging from 4 mApp to 26 mApp at a plurality of contact surfaces with the nerve trunk for an interval sufficient to effect substantially immediate pain relief in the patient, and (b) optionally repeating step (a) as needed to ameliorate nerve pain.

24. The method of claim 23 where the sensory peripheral nerve diameter is up to 12 mm.

25. The method of claim 23 applied to a nerve selected from the group consisting of an ilioinguinal nerve to ameliorate post-surgical hernia pain, an intercostal nerve to ameliorate pain from shingles, a sciatic nerve to ameliorate neuropathic diabetes pain, an occipital nerve to ameliorate migraine pain, and combinations thereof.

26. A method of ameliorating overactive bladder in a patient in need thereof, the method comprising (a) connecting a waveform generator operatively to the nerve cuff electrode of claim 1 implanted in a patient and contacting a trunk of a pelvic nerve in the patient resulting in prevention of action potential transmission in the pelvic nerve upon application of a waveform having a frequency of at least 5 kHz up to 50 kHz where the frequency blocks but does not stimulate and is not used to generate an action potential in the pelvic nerve but rather to block conduction of an action potential at one of a voltage ranging from 4 Vpp to 20 Vpp, or a current ranging from 4 mApp to 26 mApp at a plurality of contact surfaces with the nerve trunk for an interval sufficient to effect substantially immediate amelioration, and (b) optionally repeating step (a) as needed.

* * * * *